United States Patent [19] [11] 4,049,728
Kraus et al. [45] Sept. 20, 1977

[54] HYDROFLUORINATION PROCESS
[75] Inventors: Wayne P. Kraus; Thomas Hutson, Jr., both of Bartlesville, Okla.
[73] Assignee: Phillips Petroleum Company, Bartlesville, Okla.
[21] Appl. No.: 669,538
[22] Filed: Mar. 23, 1976
[51] Int. Cl.² .............................................. C07C 19/08
[52] U.S. Cl. ................................................. 260/653.6
[58] Field of Search ....................... 260/653.6; 203/91
[56] References Cited
U.S. PATENT DOCUMENTS 2,434,000  1/1948  Matuszak ........................... 260/653.6
2,456,435  12/1948 Matuszak ........................... 260/653.6
2,832,812  4/1958  Belden .............................. 260/653.6
3,888,935  6/1975  Sobel ............................... 260/653.6

Primary Examiner—Delbert E. Gantz
Assistant Examiner—J. Thierstein

[57] ABSTRACT

Improved hydrofluorination process with minimum polymer and heavy oil formation comprising carrying out the hydrofluorination of olefins with HF in a paraffinic diluent followed by low pressure and low temperature fractional distillation. In a preferred embodiment, normal butane or normal pentane is used as a diluent in the hydrofluorination, and the entire process of hydrofluorination and recovery is carried out at temperatures below about 80° F (26.7° C).

9 Claims, 1 Drawing Figure

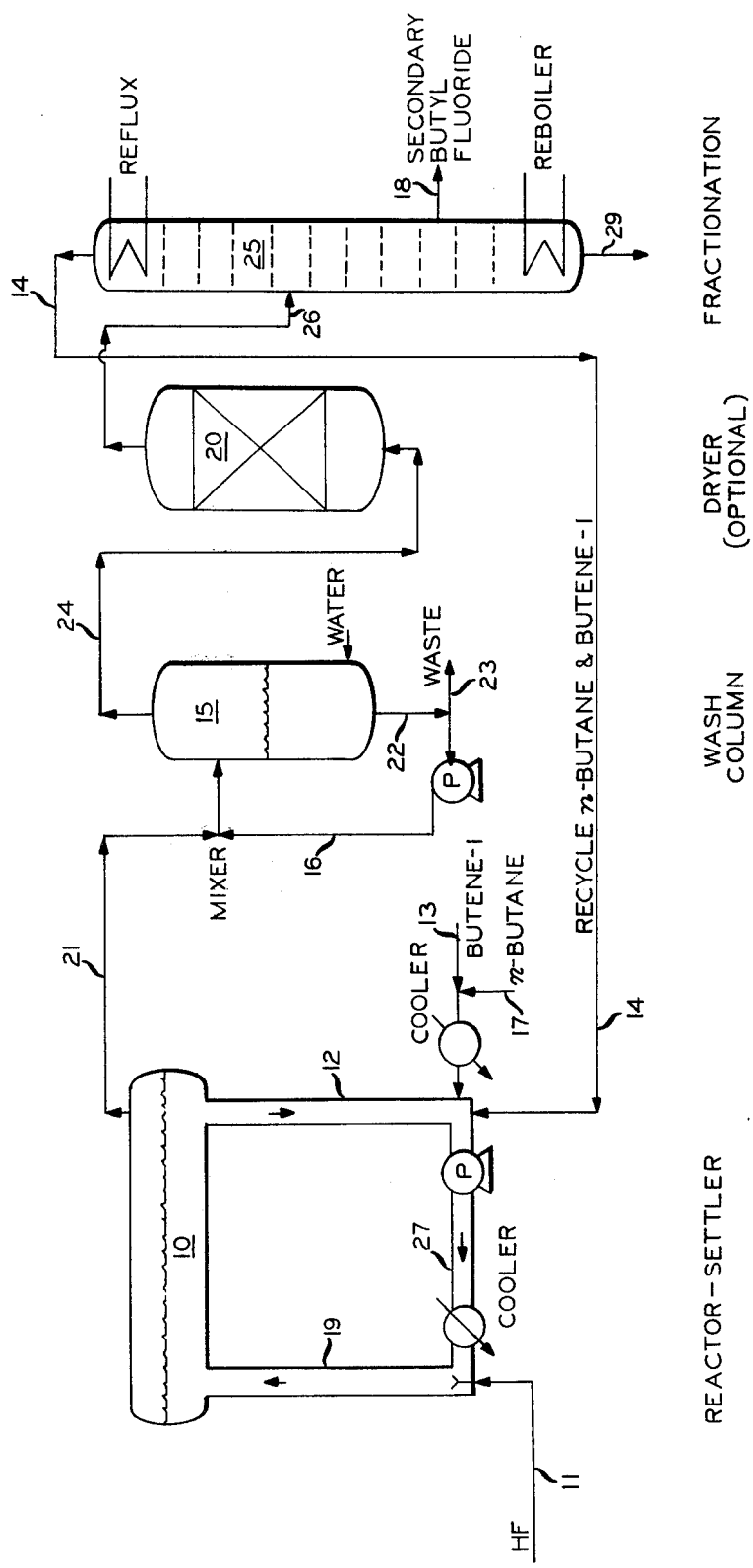

HYDROFLUORINATION PROCESS

This invention relates to an improved process for the production of alkyl fluorides. In accordance with another aspect, this invention relates to an improved process for hydrofluorinating olefins with HF using a paraffinic hydrocarbon diluent to minimize polymer and heavy oil formation. In accordance with another aspect, this invention relates to an improved recovery process for separating alkyl fluorides from olefins, paraffins, and HF by subjecting the mixture to fractional distillation under reduced pressures and fractionation temperatures below about 80° F ( 26.7° C). In accordance with a further aspect, olefins are hydrofluorinated to high purity alkyl fluorides by carrying out the hydrofluorination in a $C_4$ or $C_5$ paraffin diluent followed by low pressure and low temperature fractionation of the hydrofluorination effluent to minimize polymer and heavy oil formation.

It is known in the art to hydrofluorinate olefinic hydrocarbons with HF to produce alkyl fluorides. One problem encountered in the hydrofluorination of olefins is that during hydrofluorination or subsequent separation there are produced high boiling alkyl fluorides which are undesirable, particularly when the alkyl fluorides are used to HF alkylate an isoparaffin to produce alkylate. The present invention overcomes this problem by avoiding the production of polymer and heavy oils during the hydrofluorination and subsequent separation steps. This is accomplished according to the invention by carrying out the hydrofluorination and subsequent separation at a low temperature plus hydrofluorinating the olefin in the presence of an inert diluent.

Accordingly, an object of this invention is to provide an improved process for hydrofluorinating olefins.

Another object of this invention is to hydrofluorinate olefins under conditions to minimize polymer and heavy oil formation.

A further object of this invention is to recover alkyl fluorides from mixtures containing same under distillation conditions minimizing polymer and heavy oil formation.

Other objects and aspects, as well as the several advantages of the present invention will be apparent to those skilled in the art upon a study of the specification, the drawing, and the appended claims.

In accordance with the invention, an improved process for the production of high purity alkyl fluorides is provided which comprises hydrofluorinating olefins with HF, in a paraffinic diluent, followed by separation of the reaction effluent under fractional distillation conditions including a pressure below atmospheric and a temperature sufficiently low to minimize polymer and heavy oil formation during distillation.

In accordance with another embodiment, hydrofluorination of $C_4$ olefins with HF is carried out in either n-butane or n-pentane diluent followed by fractional distillation of the reaction effluent at a pressure below atmospheric and a temperature below about 80° F (26.7° C) and recycle of any unreacted $C_4$ olefins and diluent to the hydrofluorination.

In one preferred embodiment of the invention, a portion of the effluent from hydrofluorination is subjected to a water or caustic wash to remove HF prior to subjecting the reaction effluent to fractional distillation. The water or caustic wash further minimizes the problem of polymer and heavy oil formation.

In the first step of the present process, i.e., the hydrofluorination, a suitable olefin-containing hydrocarbon stream feed that can be employed includes, generally, $C_3$-$C_6$ monoolefins. Such olefins include propylene, 1-butene, 2-butenes, isobutylene, amylenes, and the like. It is presently preferred to use $C_4$ olefins, especially 1-butene, for the hydrofluorination. The hydrofluorination temperature is sufficient to hydrofluorinate the olefinic hydrocarbons present in the feed to produce alkyl fluorides but preferably low enough to avoid polymer and heavy oil formation and generally will be in the range of −40° to 50° F (−40° to 10° C) or more, although for best results temperatures below about 40° F (4.4° C) are employed. The pressure is ordinarily sufficient to maintain liquid phase conditions and can range from about atmospheric to 200 psig, depending upon diluent. The period of time for carrying out the reaction can range from 0.1 minute to, say, 200 minutes or more. The liquid volume ratio of hydrocarbon to HF can be in the range of 0.01 to 0.5.

In accordance with the invention, the hydrofluorination is carried out in the presence of an inert diluent comprising normal paraffins having from 3 to 6 carbon atoms. It is presently preferred to use n-butane or n-pentane. The amount of diluent present based upon olefin with be a mol ratio of about 1:1 to about 5:1.

The equipment used for carrying out the hydrofluorination reaction is such that good mixing is achieved between the introduced HF and recycle and fresh hydrocarbon reactants. Various means can be provided for dispersing HF, for example, as fine droplets into a liquid hydrocarbon mass which includes the reactant olefins and normal paraffinic diluent.

The reaction effluent removed from the hydrofluorination reactor comprising alkyl fluorides, unreacted olefin, paraffinic diluent, and HF is subjected to fractional distillation at a pressure below atmospheric and a temperature sufficiently low to avoid any substantial production of polymer and heavy oils. In general, the minimum temperature employed in the entire system, i.e., hydrofluorination and subsequent recovery steps, is below about 80° F (26.7° C) and for best results below about 50° F (10° C). Secondary butyl fluoride, has at atmospheric pressure, a boiling point of about 75° F (about 24° C) and will decompose at about 80° F (about 26.7° C). Pressure is selected so that separation of secondary butyl fluoride can be effected at a temperature (kettle) of less than about 80° F (26.7° C). Bottoms pressure in fractionator is less than about one atmosphere absolute.

In order to achieve further reduction in polymer and heavy oil formation, the hydrofluorination effluent prior to fractional distillation is water or caustic washed under conditions to substantially remove HF remaining in the effluent. Although water alone can be used, often the water is mildly basic by the addition of an alkali metal hydroxide such as KOH or NaOH. The water to hydrocarbon ratio in the wash tower is in the range of 1:1 to 10:1. The pressure in the wash tower is usually sufficient to maintain liquid phase conditions which can include a pressure in the range of, say, 100 to 200 psig, to insure liquid hydrocarbon phase is maintained. Temperature below about 80° F (26.7° C) is used in the water wash or caustic wash. Weight percent, e.g., NaOH, caustic in water is usually one to five percent, when water alone is not used for wash.

A better understanding of the invention will be obtained upon reference to the accompanying drawing which diagrammatically illustrates one preferred embodiment of the invention.

Referring now to the drawing, anhydrous HF is introduced by line 11 into a lower portion of vertical hydrofluorination reactor 19. Butene-1 introduced by line 13 and n-butane diluent introduced by line 17 are combined and mixed with a portion of the hydrofluorination effluent in line 12, and the total mixture is passed by way of line 27 into a lower portion of vertical reactor 19 and contacted with HF introduced by line 11. The temperature maintained in reactor 19 is about 20° F (−6.7° C) and sufficient pressure used to maintain liquid phase conditions. Suitable nozzles or other apparatus can be provided in the lower portion of vertical reactor 19 for providing intimate contact between HF and the hydrocarbon mass introduced by line 27.

The hydrofluorination reaction effluent enters separator 10 from which the HF portion is removed by line 12 for recycle and recontact in reactor 19, as previously described.

The hydrocarbon-alkyl fluoride portion of the hydrofluorination reaction effluent comprising secondary butyl fluoride, unreacted butene-1, n-butane diluent, and some HF is removed by line 21 and passed to water wash tower settler 15 wherein the reaction effluent is contacted with water or basic water or slightly basic water to remove HF from the reaction effluent. A bottoms stream comprising water and absorbed HF (or the salt when a caustic solution is used) is removed by line 22, a portion of which is recycled via line 16 for contact with the liquid in line 21 prior to introduction into tower 15. A mixer (e.g., inline mixer) is used for contact between the two liquid phases. A slip stream 23 of aqueous solution is removed from the system. Makeup water or caustic solution is added to the bottom aqueous phase in vessel 15, as shown.

Water-washed effluent is removed from the tower 15 by line 24 and passed, optionally, through a dryer 20 which contains a suitable drying agent such as $Al_2O_3$ or the like. A silica-free desiccant is used to preclude $SiF_4$ formation.

The dried reaction effluent substantially freed of HF is passed by way of line 26 to fractional distillation zone 25 wherein the reaction effluent is subjected to fractional distillation conditions including pressures below atmospheric and a temperature preferably below 50° F (10° C). The fractionation column 25 has reboil and reflux shown schematically.

A stream comprising unreacted butenes and n-butane diluent is removed overhead by line 14 and recycled to the hydrofluorination step and is combined with the recycle in line 12 for return to reactor 19. A side stream comprising high purity 2-fluorobutane is removed by line 18 which can be passed to conventional HF alkylation (not shown) wherein the alkyl fluoride is contacted with an isoparaffin under conditions which produce alkylate. A bottoms residue stream is removed from fractionator 25 by line 29 for further use as desired.

The following calculated example will better illustrate the invention. In this example, butene-1, n-butane diluent, and HF are contacted under hydrofluorination conditions, and the effluent is water washed and fractionally distilled into an overhead fraction which is recycled to hydrofluorination, and a high purity butyl fluoride is recovered as product. The reactants and conditions used in the various steps of the process are as set forth below.

| TYPICAL OPERATION: | | |
|---|---|---|
| Reactor (19): | | |
| Temperature, ° F | | 20 (−6.7° C) |
| Pressure, psig* | | 175 (1190 kPa) |
| Residence time, min. | | 90 |
| Water Wash (15): | | |
| Temperature, ° F | | 70 (21.1° C) |
| Pressure, psig* | | 150 (1030 kPa) |
| Fractionator (25): | | |
| Temperatures, ° F: | | |
| Top | | −25 (−31.7° C) |
| Bottom | | 38 (3.3° C) |
| Pressure, mm Hg | | 300 (39.2 kPa) |
| Feed Rates: | | |
| (11) | Anhydrous HF, gpm | 16.5 (62.5 liters/min.) |
| (12) | Recycle HF, gpm | 820 (3104 liters/min.) |
| (13) | Butene-1, gpm | 63.9 (242 liters/min.) |
| (14) | Recycle n-butane, gpm** | 63.9 (242 liters/min.) |
| (16) | Wash liquid/ hydrocarbon***, volume ratio | 5:1 |
| (18) | 2-Fluorobutane, gpm | 52.9 (200 liters/min.) |

*To maintain liquid phase.
**Shown on the drawing is addition of outside n-butane. This is for startup and any makeup of n-butane needed. The source of on-stream n-butane is from recycle via conduit 14.
***Can be slightly alkaline.

We claim:
1. A process for the production of high purity alkyl fluorides with minimum polymer and heavy oil formation which comprises:
 a. hydrofluorinating an olefin with HF in a normal paraffin diluent wherein the normal paraffin contains from 3 to 6 carbon atoms under liquid phase hydrofluorination conditions and a temperature below about 80° F (26.7° C) to produce an effluent comprising alkyl fluoride, unreacted olefin, normal paraffin diluent, and HF;
 b. separating said effluent into an HF phase portion and a hydrocarbon phase portion;
 c. subjecting the hydrocarbon phase portion of said effluent to fractional distillation conditions at a pressure substantially below atmospheric and a temperature below about 80° F (26.7° C) which is sufficiently low to prevent polymer and heavy oil formation and to separate a first stream comprising alkyl fluoride and a second stream comprising unreacted olefin, and diluent; and
 d. recycling said stream containing unreacted olefin and diluent to step (a) for reuse in the process.

2. A process according to claim 1 wherein the amount of paraffin diluent based on olefin present during said hydrofluorinating is in the mol ratio of 1:1 to 5:1 and said hydrofluorination conditions include a temperature in the range of −40° to 50° F (−40° to 10° C) to avoid polymer formation.

3. A process according to claim 1 wherein said portion of said effluent prior to being subjected to fractional distillation is subjected to a water or caustic wash to remove unreacted HF therefrom and further minimize polymerization of alkyl fluoride to heavy oils.

4. A process according to claim 1 wherein the HF portion of said effluent is recycled to step (a) to hydrofluorinate olefin and produce alkyl fluoride and further wherein in step (a) the fresh or reactant liquid HF is introduced into the olefin and paraffin diluent as fine droplets to improve contact between the HF and reactant olefin.

5. a process according to claim 1 wherein said olefin is butene-1 and said diluent is n-butane or pentane.

6. A process according to claim 1 which comprises:
   a. hydrofluorinating butene-1 with HF in n-butane diluent to produce an effluent comprising 2-fluorobutane or secondary butyl fluoride, unreacted butene-1, n-butane, and HF;
   b. separating overhead from said fractional distillating n-butane and unreacted butene-1, a side stream comprising 2-fluorobutane, and a bottoms residue; and
   c. recycling said overhead to step (a) for reuse in the process.

7. A process according to claim 6 further comprising the steps of subjecting said hydrocarbon phase portion of said effluent to a water or caustic wash to remove unreacted HF prior to fractional distilling in step (b) and recycling the HF phase of said effluent to step (a) to hydrofluorinate butene-1 and produce 2-fluorobutane.

8. A process according to claim 7 wherein the amount of n-butane present in step (a) based on butene-1 is in the mol ratio range of 1:1 to 5:1 and the distillation temperature in step (b) is below about 50° F (10° C).

9. A process according to claim 1 which comprises:
   a. hydrofluorinating butene-1 with HF in a pentane diluent at a temperature below about 40° F (4.4° C) to produce an effluent comprising 2-fluorobutane, unreacted butene-1, pentene, and HF;
   b. separating said effluent into a yield hydrocarbon phase portion and a recycle HF phase portion;
   c. recycling said recycle HF phase portion of step (b) to step (a) to hydrofluorinate butene-1 and produce 2-fluorobutane;
   d. subjecting said yield portion to water or caustic wash to remove unreacted HF therefrom and minimize polymerization of 2-fluorobutane to heavy oils;
   e. fractionally distilling the washed portion obtained in step (d) reduced in HF under conditions of a pressure substantially reduced below atmospheric and a temperature below about 50° F (10° C) to minimize heavy oil production and to separate unreacted butenes overhead, 2-fluorobutane as a side stream, and pentane as bottoms; and
   f. recycling said overhead and said bottoms to step (a) for reuse in the process.

* * * * *